United States Patent [19]

Lim et al.

[11] 4,324,683
[45] Apr. 13, 1982

[54] ENCAPSULATION OF LABILE BIOLOGICAL MATERIAL

[75] Inventors: Franklin Lim, Richmond; Richard D. Moss, Chester, both of Va.

[73] Assignee: Damon Corporation, Needham Heights, Mass.

[21] Appl. No.: 606,166

[22] Filed: Aug. 20, 1975

[51] Int. Cl.³ .......................... B01J 13/02; A61K 9/50
[52] U.S. Cl. ...................................... 252/316; 264/4; 424/32; 424/36; 424/94; 424/101
[58] Field of Search .............. 252/316; 264/4; 424/32, 424/101, 94

[56] References Cited

U.S. PATENT DOCUMENTS 3,429,827 2/1969 Ruus ..................................... 252/316
3,577,515 5/1971 Vandegaer ...................... 252/316 X

FOREIGN PATENT DOCUMENTS 873815 6/1971 Canada ............................... 252/316
1600988 9/1970 France ............................... 252/316

OTHER PUBLICATIONS

Griffin: "Calculation of HLB Values of Non-Ionic Surfactants", The American Perfumer & Essential Oil Review, May 1955, pp. 26–29.

Primary Examiner—Richard D. Lovering
Attorney, Agent, or Firm—Kenway & Jenney

[57] ABSTRACT

A two step interfacial polymerization process for encapsulating operative chemically active substances in high quality semipermeable membranes. An emulsion is formed wherein the discontinuous phase contains the substance to be encapsulated and a first monomer. When a second monomer is added to the continuous phase, an imperfect membrane forms about the droplets of the discontinuous phase. Removal of the continuous phase, followed by resuspension of the raw microcapsules and addition of a second portion of second monomer, causes further polymerization strengthening the membranes and "patching" macroporous defects in them. The choice of solvents and control of reaction conditions such as pH, maximize the yield of operable labile substance encapsulated. A method of encapsulating a very high concentration of hemoglobin is also disclosed. Adaption of the two step process provides a method for forming and controlling the pore sizes in the membranes of a number of known prior art encapsulation processes.

39 Claims, No Drawings

ENCAPSULATION OF LABILE BIOLOGICAL MATERIAL

BACKGROUND OF THE INVENTION

This invention relates to a process for encapsulating chemically active substances, and particularly to encapsulating labile biological substances such as enzymes and hemoglobin, in a semipermeable membrane which will retain the encapsulated material, yet will freely allow smaller molecules to pass through the membrane to react with the encapsulated material and reaction products to pass out. It also relates to a method of controlling the size of the pores in the semipermeable membranes of the capsules.

Microencapsulation technology has grown rapidly in recent years and has found many applications. Attempts have been made, with varying degrees of success, to encapsulate biologically active substances such as hemoglobin, carbonic anhydrase, urease, asparginase, lactate dehydrogenase (LDH), glutamate oxaloacetate transaminase (GOT), chemically active materials such as ion exchange resins and activated charcoal, and various other enzymes and chemically active substances. Microcapsules of this nature have already proven to have great utility in, for example, artificial kidneys and fixed enzymes system, and show great promise in a number of other areas. As an example, U.S. Pat. No. 3,522,346 to Thomas M. S. Chang, discloses non-thrombogenic microcapsules which can be utilized, when fabricated about enzymes or detoxicants and placed in an extracorporeal shunt, to introduce oxygen, medicaments, enzymatic substances, and the like into the blood stream at controlled rates.

In *Artificial Cells,* by Thomas M. S. Chang, (Charles C. Thomas, Publisher; Springfield, Ill. 1972) a process for encapsulating biologically active materials in a semipermeable membrane is disclosed. The technique involves dissolving the material to be encapsulated and a monomer in water, and forming an emulsion with the water as the discontinuous phase. When a second monomer capable of polymerization with the first is dissolved in the continuous phase of the emulsion, a polymerization occurs at the interface of the two phases, and a membrane is formed around the typically colloidal sized droplets of solution.

This procedure has drawbacks and limitations which curtail its potentially wide applicability and commercial success. Since many biologically active substances, e.g. enzymes, are extremely labile, the relatively harsh reaction conditions necessary for polymerization often result in a very low yield of operable encapsulated material. Encapsulation of even relatively hardy enzymes, such as urease, is characterized by yields at best between 35 and 40 percent. At one or more steps in the process, much of the encapsulated material is denatured.

U.S. Pat. No. 3,522,346 (T. M. S. Chang) relates to microcapsules of controlled permeability. The process therein disclosed involves encapsulating aqueous compositions in membranes of controlled size, thickness, and permeability. Droplets of an aqueous composition are dispersed in an organic liquid medium immiscible therewith and a component soluble in the organic liquid medium and capable of reacting with a component of the hydrophilic composition is added to the dispersion thereby produced to form a macromolecular membrane by interfacial coacervation, polymerization, or condensation at the surface of the droplets. Typically, a polymer, condensation product, or a component thereof is added to the organic liquid and the membrane is formed about the droplets by interaction of the polymer, condensation product or component with a component of the dispersed droplets, which may be a precipitant, a condensation or polymerization catalyst, or a compound of the eventual condensation product. The effective pore size of the encapsulating membrane is a function not only of the membrane composition but also of the thickness of the membrane and is selected in accordance with the intended use of the capsules. By suitable choice of operating conditions, pore size may be varied, but the reaction condition necessary to ensure sufficiently strong yet selectively permeable membranes are in any case difficult to control and in some cases unknown. Also, the procedure produces capsules generally having membranes with erratic uniformity and porosity, many of which are useless for their intended purpose.

It is therefore an object of this invention to provide a process wherein a large variety of enzymes, other labile biological material, and many chemically active substances can be encapsulated in their active state, and to provide a higher yield of operative substance when so encapsulated.

A further object of the invention is to provide a method for forming very strong semipermeable membranes around any of a large number of labile biological materials.

Still a further object of the invention is to provide a method of manufacturing enzyme containing microcapsules wherein the microcapsule membrane has a more uniform degree of semipermeability, that is, to provide capsules with uniform walls without porous defects and with a pore size range such that the encapsulated material cannot escape from the interior of the capsule yet can readily react with substances in the environment in which the capsules are placed.

Another object of the invention is to provide a process for encapsulating a large variety of chemically active substances in a high quality semipermeable membrane by utilizing a variety of different polymer systems and different interfacial polymerization techniques. Yet another object of the invention is to provide a general process having some variable parameters, values for which may be selected to suit a particular substance to be encapsulated, to vary the nature of the capsule membrane, and to maximize the yield of operative encapsulated material.

Still another object of the invention is to provide a method of encapsulating a high concentration of hemoglobin in a capsule permeable to oxygen, carbon dioxide, and other small molecules.

Yet another object of the invention is to provide a method of controlling capsule membrane pore size to an improved degree, the method having wide applicability to a large variety of encapsulation techniques.

Still another object of the invention is to provide strong semipermeable microcapsules with membranes having pore sizes falling within any one of a number of size ranges, hence being selectively permeable to molecules having dimensions smaller than the upper limit of the range chosen.

SUMMARY OF THE INVENTION

In general, the invention is characterized by a two-step polymerization process using at least two monomers which will polymerize, one of which is soluble in a hydrophobic solvent, the other of which is soluble in a hydrophilic solvent or water. First, a hydrophilic solution is prepared, preferably with water, by dissolving the material to be encapsulated in the water together with a first monomer. Since many monomer solutions have a pH which would denature any labile biological substances, the monomer solution often must be buffered to a pH range between 5 and 9 before labile biological material is added.

A hydrophobic organic liquid is then prepared which has the following properties. First, the solubility of the second monomer which is to be used in the polymerization should be very high in this hydrophobic organic liquid. Second, the hydrophobic liquid should have a slight affinity for the first monomer. Third, the hydrophobic solvent should be such that the hydrophilic solvent, when added to it, will form a good emulsion.

The two solvents are then added together and emulsified, the hydrophilic solvent, typically, being the discontinuous phase. Emulsification can be accomplished by any one of several well-known techniques, usually with the aid of an emulsifying agent. The size of the droplets produced dictates the size of the microcapsules formed.

When the desired droplet size range has been achieved, the second monomer is added to the emulsion, and polymerization, condensation, or polyaddition, occurs at the interface of the two-phased system. Because the first monomer, dissolved primarily in the discontinuous phase, is slightly soluble in the continuous, hydrophobic organic phase, some diffusion occurs into the continuous phase. The microcapsule membrane forms across this interface zone as the polymerization proceeds. The forming membrane limits the further diffusion of the first monomer into the continuous phase, with the membrane characteristics very dependent on the detailed sequence of random encounters between the monomers.

Generally, the membranes produced to this point are macroporous with successful semipermeable membranes occurring only under exceptional conditions which are difficult to control. It is believed that the problem results from the presence of defects in the membranes which result in macroporous holes through the membranes after the reaction is quenched and the capsules are washed. In the prior art, this is overcome only by continuing the polymerization, condensation, or polyaddition for long enough to close these large defects, which simultaneously closes the smaller pores. Acceptable capsules thus are believed to result only over a narrow range of polymer formation in which the defects are closed and the smaller pores are still open.

However, it has been discovered that if such raw microcapsules are separated from the continuous phase, resuspended in a quantity of different hydrophobic liquid in which the solubility of the first monomer is greatly reduced, and then exposed again to the second monomer, the same polymerization reaction occurs at a much slower rate over a much narrower interface zone lying only within the interstices of the raw capsule membrane. This results in the "patching" of the macroporous defects in the capsule's wall, decreasing the pore size, and strengthening the membranes.

It is believed that this second polymerization reaction bridges selectively more across the larger pores where the first monomer diffuses closer to the continuous phase, and that this "patching" proceeds substantially without significant increase in the capsule wall thickness. By contrast, the continued use of the first solvent increases the wall thickness, decreasing the permeability of most of the membrane for the sake of sealing the defects.

According to another aspect of this invention, it has been found that this secondary polymerization technique is useable with a large number of known encapsulation processes to form semipermeable capsules and to control the pore sizes thereof.

According to another aspect of this two-step polymerization process, it is possible to choose the second monomer for use in the continuous phase which, in conventional procedures, would quickly denature labile biological materials sought to be encapsulated. The technique for avoiding such denaturing involves controlling relative concentration of solutes in the continuous and discontinuous phase so that the concentration of the second monomer in the continuous phase is kept to less than optimal values, and the solutes in the discontinuous phase are in high concentration. In this situation, diffusion of the second monomer into the discontinuous phase is inhibited and denaturing of the labile biological material is minimized, but a macroporous, poorly formed, and clearly unsatisfactory capsule membrane is produced. However, in the second polymerization step, the concentration of the second monomer in the continuous phase of the resuspension may be safely increased (since the encapsulated material is now protected by the raw capsule membrane) to strengthen the capsule membranes and render them semipermeable.

According to another aspect of the invention, the second monomer is added to the emulsion in the first polymerization step, not all at once to initiate polymerization, but rather in fractions, at regular time intervals, over the duration of the polymerization. This technique maintains the concentration of the second monomer at the interface at a more constant optimum level at all times in the formation of the first coarse membrane and thus inhibits diffusion of the second monomer into the discontinuous phase and increases the yield of operable labile biological material. This technique is also quite useful for systems in which hydrolysis of the chosen second monomer is a competing reaction with the polymerization.

In one important embodiment, the first monomer is a diamine and the second monomer is a diacid halide; the initial hydrophobic solvent is a solution comprising 80% cyclohexane and 20% chloroform; and in the resuspension, the hydrophobic liquid is pure cyclohexane. The diamine is essentially insoluble in cyclohexane, and slightly soluble in chloroform.

When encapsulating hemoglobin, it has been discovered that if the red blood cells are dehydrated by exposure to hypertonic saline solution, a hemoglobin solution with concentrations up to 30 g/dl may be prepared, and the high salt concentration inhibits diffusion of water molecules into the discontinuous phase where they react with molecules of the second monomer, rendering them inoperable.

Since it is well known that many labile biological materials rapidly denature in highly acidic or basic environments, at all stages of the novel encapsulation process, the pH of the immediate environment of the material sought to be encapsulated should be kept at least within the range of 5 to 9. When a diamine is used as a first monomer, this is accomplished by bubbling $CO_2$ through the diamine solution before it is added to the labile biological material. The diamine solution, which typically has a pH on the order of 11.5, is converted to diamine carbonate with a typical pH of about 8.6–8.7. If saturated with $CO_2$ and stored beneath 100% $CO_2$ gas, this solution can be brought to a pH of about 8.4.

By contrast, the prior art utilized the weak $NaHCO_3$-$Na_2CO_3$ buffer system, i.e., the salts of a strong base and the weak acid, where the present invention has used the weak acid itself. The resulting pH of the prior art, buffered diaminehemolysate solution is pH 11.

A principle advantage of the present technique for the immobilization of biologically and/or chemically active materials to form solid or pseudo-solid reactors, is that the materials are encapsulated in bulk without direct competition with impurities for available binding sites. Thus highly active capsules can be made from relatively poorly purified materials. In addition, the active materials are protected from attack by microorganisms often responsible for the inactivation or inhibition of such reactor components.

DESCRIPTION OF THE PREFERRED EMBODIMENT

A first aspect of this invention utilizes a novel variation in the well-known process for microencapsulation known generally as "interfacial polymerization". Two mutually immiscible solvents are chosen, one being hydrophobic, the other being hydrophilic or, preferably, water. The material to be encapsulated and a first monomer are dissolved in water, the two solvents are mixed, and then the mix is emulsified, the hydrophobic solvent being the continuous phase. The size of the colloidal droplets determines the size of the microcapsules to be produced. Emulsification may be accomplished by any of the well-known emulsification techniques such as, for example, using a blender, and is usually done with the addition of an emulsifying agent. Since the size of the droplets produced in any given technique will vary within a specific range, a filter may be used to separate oversized capsules made in any given run to minimize differences in capsule diameter. For a more detailed disclosure of the method for varying capsule size, reference should be made to Thomas M. S. Chang, *Artificial Cells*, chapter 2.

When droplets of sufficient size have been produced, a second monomer capable of forming a polymer with the first monomer by polycondensation or polyaddition is introduced into the suspension. Polymerization occurs only at the interface of the two-phase system. Obviously, the monomer must be chosen from among those which exhibit suitable solubility properties in the solvents chosen.

To maximize yield of operable biological material enclosed within the capsules, reaction conditions must be carefully controlled so that the generally sensitive material will not denature to any significant extent during the polymerization. Accordingly, it has been discovered that a most critical factor in obtaining a high yield of operable encapsulated material is the pH of the discontinuous phase. To ensure against denaturing of labile material, the pH must be controlled at all times during the process, generally within the range of 5 and 9. The solvents must be chosen, especially the hydrophilic one which dissolves the encapsulating material, from among those which will not quickly denature the material to be encapsulated. The choice will be well within the ability of men skilled in the art after they have read the disclosure. To facilitate proper dispersion and separation, the two solvents should have specific gravities slightly different from each other.

Polymerizations which occur in a pH environment which is hostile to the particular chemically active substance sought to be encapsulated should not be used for that substance. However, many monomers, which in solution have a natural pH capable of denaturing most labile biological material, may be buffered to within the above disclosed pH range without affecting their activity. Other monomers can be used without buffering, depending on their natural pH and the nature of the material sought to be encapsulated. For highly alkaline monomers, passing $CO_2$ gas through the solution is a preferred method of bringing the pH within the non-denaturing range.

According to a second aspect of the invention, it has been discovered that a much stronger capsule membrane having fewer imperfections and using a minimal degree of polymerization can be produced by a two-step polymerization. In this regard, it has been discovered that the capsule membranes produced by the above-described single step process are often macroporous, uneven, and vary considerably in strength and thickness. However, if the polymerization at the interface of the emulsified system is quenched by removal of the continuous phase, and the capsules are then resuspended in fresh solvent with reduced solubility for the first monomer, an additional portion of the second monomer added to the resuspension will cause further polymerization which will strengthen the membranes, cause the larger pores of the membranes to fill in preferentially, and thereby avoid the macroporous condition. The process hence produces a high quality, semipermeable membrane by the use of a second, minimal amount of polymerization, the latter being used to maximum additional advantage to fill in the membrane imperfections.

Further refinements of this two-step polymerization process enabled control of the strength, thickness and porosity of the membranes to an improved degree. If the hydrophobic solvent comprising the continuous phase of the emulsion is chosen such that the first monomer is slightly soluble therein, monomer from the droplets diffuses slightly into the continuous phase. This results in a relatively thick phase boundary and an equally thick and usually porous membrane, formed wherever the two monomers come into contact. Generally, the greater the solubility of the first monomer in the continuous phase, the more macroporous the membrane produced. If, on the other hand, the first monomer is much less soluble in the continuous, hydrophobic phase, the boundary between the phases is sharp, and a thin, dense, and usually microporous membrane results. When the partly formed capsules are resuspended, a different solvent is used having a different solubility for the first monomer than the solvent used as the discontinuous phase in the first polymerization. When a macroporous membrane has been produced in the first polymerization, a solvent in which the first monomer is essentially insoluble is used in the second polymerization, and has the effect of hardening the membranes. It is believed that in the second polymerization step, the two precursers to the polymer meet only within the weak spots of the imperfect membrane produced up to that point, i.e, where there is preferential diffusion of the first monomer towards the solvent. Thus, more polymer is formed to fill in the larger pores.

According to another aspect of the invention, the concentrations of the monomers in their respective solvents can be controlled to further advantage. If, for example, the second monomer, dissolved in the hydrophobic, continuous phase of the emulsion, has the property of denaturing the material sought to be encapsulated, the first monomer, dissolved in the discontinuous phase, may be introduced at a high concentration relative to the second, on the order of 100 to 1, to prevent any migration of the denaturing monomer into the droplets of solution during the first polymerization. This technique often produces a highly porous microcapsule, but, in the second polymerization step, the concentration of the second monomer may be safely increased, and if a proper solvent is used, the capsules will be strengthened and rendered microporous by selectively bridging across the larger pores with a thinner membrane, as explained above, without seriously affecting the encapsulated material.

According to another aspect of the invention, it has been found that the concentration of hemoglobin encapsulated can be increased significantly if red cells used to make hemoglobin hemolysate are thoroughly washed in hypertonic saline. In addition, the relatively high salt concentration in the aqueous, discontinuous phase of the emulsion aids the interfacial polymerization of the first monomer by limiting the solubility of water in the organic phase containing the second monomer, which, typically, is rapidly decomposed on exposure to water. It is believed that the reaction products of such hydrolysis of the second monomer contribute to the imperfections of the membrane if not removed in the separation step.

The invention will be further clarified and understood by the following examples.

EXAMPLE 1

Red cells from expired blood blank whole human blood were separated and then washed two times in twice their volume of hypertonic saline (1.5 g/dl) by centrifuging in a refrigerated centrifuge at 2800 xg for five minutes. Hypertonic saline was used to remove water from the cells in order to produce the highest possible concentration of hemoglobin after the lysis of the cells. A third centrifugation for 15 minutes at 2800 xg served to pack the cells. As much saline as possible was removed from the packed cells which were then lysed by shaking vigorously with one ml anhydrous ether per 10 ml packed cells. This mixture was centrifuged at 1000 xg for 20 minutes and the cell debris and ether which rise to the top removed. Hemoglobin concentration was checked by measuring the absorbance of 10 $\mu$l of the hemolysate in 4.0 ml of isotonic saline at a wavelength of 540 nm. The absorbance readings from all property prepared hemolysate solutions were between 0.7 and 0.8, which correspond to a concentration of 28 to 32 g/dl. Hemoglobin concentrations greater than 30 g/dl crystalized and precipitated on storage at refrigerator temperature (4° C.). The hemolysate could be used for at least a week if refrigerated.

Hexanediamine carbonate solution was prepared by bubbling carbon dioxide into a 3 M solution of 1,6 hexanediamine (Eastman Kodak Co.) until the pH reached 8.5. This required about 15 grams of $CO_2$ per 100 ml of solution.

4,4' diamino-biphenyl-2,2' disulfonic acid (DBDSA) (Technical Grade-Eastman Kodak Co.) was prepared by adding approximately 50 grams of DBDSA in 800 ml of deionized water containing 50 ml of 6 M NaOH. The solution was filtered to remove any remaining solids and the DBDSA precipitated by adding 70 ml of 50% v/v HCl. After the crystals had settled, as much of the purple liquid as possible was poured off; then 500 ml 10% v/v HCl was added. The crystals were collected in a Buchner funnel and washed three times with deionized water; then washed twice with acetone and dried. The product was white or pale pink crystals and was stored in a brown bottle protected from light. This compound was used to form a membrane copolymer having a negative charge to prevent clumping.

Ten milliliters of hemolysate solution containing 30 g/dl hemoglobin was mixed with 10 ml of 3 M hexanediamine carbonate solution containing 2.88 grams of DBSA. These two monomers, when mixed, comprised the first reactant in this example. This aqueous solution was then added to 125 ml of prechilled hydrophobic organic liquid made from 100 ml of 20% chloroform--80% cyclohexane mixture and 25 ml of an emulsifying agent, SPAN-85 ®(Sorbitan trioleate).

Emulsification was then started in a prechilled blender and continued for 1 to 2 minutes.

Terephthaloyl chloride, the second monomer, required preliminary purification. Hot (nearly boiling) cyclohexane was saturated with terephthaloyl chloride (Practical grade-Eastman Kodak Co.) and the solution quickly filtered. The clear liquid was collected and allowed to cool and crystallize in a closed container. The crystals were collected with as little exposure as possible to the atmosphere and dried in a vacuum as this compound reacts with atmospheric moisture. The stock solution of terephthaloyl chloride was prepared by dissolving 10.15 grams of purified terephthaloyl chloride in 95 ml of 20% $CHCl_3$-80% $C_6H_{12}$, v/v. A 0.5 M solution resulted. This solution should be kept in a tightly sealed container and may be used for at least a month of until precipitate begins to form.

Three ml of the 0.5 M terephthaloyl chloride in 20% chloroform-80% cyclohexane organic solution were then added to the emulsion while blending at a low speed. The actual concentration ratio of diamine/diacid halide was 128 to 1, although some variation is tolerable. At the end of three minutes, the first polymerization reaction was complete and the suspension was centrifuged for 15 to 20 seconds at 400 to 500 xg. The supernatant organic liquid was then removed by aspiration.

The capsules were then resuspended in a second liquid consisting of 100 ml cyclohexane and 10 ml sorbitan trioleate. While mixing slowly, 7 ml of 0.5 M terephthaloyl chloride in 20% chloroform and 80% cyclohexane organic solution were added. This hydrophobic liquid contains only 1.0 to 1.5% chloroform versus 20% in the first organic stage. The reduced chloroform content cuts down the solubility of diamine in the solvent making a thinner membrane and patching holes in the original coarser one. The diamine/diacid halide concentration ratio was 50 to 1. Stirring was continued for 3 minutes at which time the reaction was quenched by the addition of 30 ml of 50% TWEEN-20 (sorbitan monolaurate) buffered to neutral pH with 0.3 M $NaHCO_3$.

Note that the hemoglobin-enzymes hemolysate solution was at no time exposed to a pH less than 5 or greater than 9. Hexanediamine solution has a natural pH of 11.5 and a pH of about 11 when mixed with hemoglobin. Bubbling the $CO_2$ therethrough causes the production of $H_2CO_3$ and hexanediamine carbonate. The $CO_2$ acts as a buffer and is preferred over sodium salts or weak acids. Before buffering, the sorbitan monolaurate used had a typical pH of approximately 4.5. Extended exposure to this acidic environment would denature the hemoglobin and enzymes. This can be avoided by buffering the sorbitan monolaurate to have a pH close to 7. The purpose of the sorbitan monolaurate is to facilitate transfer of the microcapsules into an aqueous medium such as saline. (see *Artificial Cells,* chapter 2) It should be noted that in this step sorbitan monolaurate tends to react slowly with the terephthaloyl chloride to produce a sticky polymer coating and, in addition, to crenate the microcapsules. A superior alternative procedure is to remove as much of the solvent as possible by centrifugation and then follow through with the above TWEEN-20 addition and subsequent separation.

Microcapsules produced by this process did not allow leakage of enzymes or hemoglobin. Half equilibrium times (t ½) for solutes of various molecular weights are given in TABLE I.

TABLE I
PERMEABILITY OF MICROCAPSULES - HALF EQUILIBRIUM TIMES

| Substance | Molecular Weight | t ½ ± SEM (sec.) |
|---|---|---|
| Glycerol | 92 | 1.75 ± .1 |
| Diacetone Alcohol | 116 | 2.5 ± .2 |
| Glucose | 180 | 4.9 ± .1 |
| Sucrose | 342 | 10.6 ± .2 |
| Tris[a] | 121 | 2.8 ± .1 |
| Bicine[b] | 163 | 6.1 ± .3 |
| CAPS[c] | 221 | 8.0 ± .5 |
| Pipes[d] | 302 | 13.0 ± .5 |

[a]Tris (hydroxymethyl) aminomethane, pH 8
[b]N,N-bis (2-Hydroxyethyl) glycine, pH 8
[c]Cyclohexylaminopropane sulfonic acid, pH 8
[d]Piperazine-N-N'-bis (2-ethane sulfonic acid), pH 8

The activity of four enzymes, lactate dehydrogenase (LDH), glutamate oxaloacetate transaminase (GOT), urease, and β-glucuronidase was measured before and after encapsulation. LDH and GOT were found naturally in the red cell hemolysate. Urease and B-glucuronidase were added to hemolysate in the form of lyophilized partially purified enzyme, available from commercial sources. The results of the comparisons for LDH, GOT, and urease are disclosed in TABLE II. Activity was measured in international units (IU) per liter of sample under conditions of the test reaction. The yields determined for β-glucuronidase were uniformly above 50%.

TABLE II

| Enzyme | Activity (IU/l) ± SEM | Retained activity[a] (%) |
|---|---|---|
| LDH | 4120 ± 90 | 55 |
| GOT | 1200 ± 80 | 66 |
| Urease | 234000 ± 8000 | 68 |

[a]The enzyme activity of the microcapsules divided by the enzyme activity of the hemolysate used in preparing the microcapsules. (% yield) (SEM = standard error for the mean)

TABLE III shows a comparison of the percent saturation of oxygen in hemolysate solution used to prepare the microcapsules with encapsulated hemoglobin, at various $O_2$ pressures.

TABLE III

| Pressure $O_2$ | Percent saturation | |
|---|---|---|
| | Hemolysate hemoglobin | Encapsulated hemoglobin |
| 5 | 7% | 5% |
| 10 | 21% | 10% |
| 15 | 46% | 20% |
| 20 | 62% | 32% |
| 25 | 74% | 45% |
| 30 | 82% | 58% |
| 35 | 89% | 68% |
| 40 | 92% | 74% |
| 50 | 97% | 83% |
| 60 | 99% | 89% |
| 70 | 99%+ | 92% |
| 80 | 99%+ | 94% |
| 90 | 99%+ | 96% |
| 100 | 99%+ | 97% |
| 110 | 99%+ | 98% |
| 120 | 99%+ | 99% |

Table IV shows the effect of varying the amount of the acid halide in the discontinuous phase of each polymerization on the porosity of microcapsules prepared in one series of tests, the porosity being measured indirectly by observing whether or not the encapsulated material leaked through the membrane. As the table clearly indicates, the concentration of the second monomer in each polymerization step is highly material to good capsule formation. Those skilled in the art will have little difficulty determining the optimal concentration ratio to be used with other polymer systems. The capsules of Table IV were made with the procedure outlined above, except that emulsification was performed in SPAN 85 alone before the mixed organic solvent was added. Results of other variants of the procedure are qualitatively similar.

TABLE IV
MICROCAPSULES MADE WITH 10 ML OF HEMOLYSATE AND VARIOUS AMOUNTS OF .5M TEREPHTHALOYL CHLORIDE

| | First Reaction Terephthaloyl Chloride | Second Reaction Terephthaloyl Chloride | Capsule Condition |
|---|---|---|---|
| 1 | 2 ml | 4 ml | Very leaky |
| 2 | 2 ml | 8 ml | Very leaky |
| 3 | 3 ml | 7 ml | No leak |
| 4 | 3 ml | 7 ml | No leak |
| 5 | 4 ml | 7 ml | No leak |
| 6 | 4.5 ml | 7.5 ml | Mod. leaky |
| 7 | 4.5 ml | 7.5 ml | Mod. leaky |
| 8 | 5 ml | 8 ml | Very leaky |
| 9 | 5.5 ml | 8 ml | Very leaky |

Microcapsules separated from the organic solvent after the first reaction were red, indicating that little or no denaturing had occurred, but leaky, and poorly formed. Increasing the terephthaloyl chloride concentration under these conditions produced microcapsules which were brown, indicating hemoglobin denaturation, and leaky. Increasing the reaction time of the first reaction up to five minutes had little apparent effect on the microcapsules, but increasing the second reaction time to more than four minutes caused the microcapsules to turn brown, indicating hemoglobin denaturation. Decreasing either reaction time one minute or more resulted in leaky microcapsules. The presence of small amounts of ethanol commonly used as a stabilizer for the chloroform can necessitate the readjustment of optimum volumes. To achieve the greatest repeatability and most reliable capsule formation, the ethanol should be removed. The chloroform used in Table IV contained some ethanol. With the ethanol extracted the optimum second reaction volume is typically 3–4 ml rather than 7. Decreasing the amount of TWEEN-20 used in the separation step resulted in poor separation of the microcapsules from the organic solvent. Microcapsules which were allowed to remain in TWEEN 20 for excessive times (>½ hour) turned brown. Microcapsules stored in unbuffered saline which has a pH of 5.5 turned brown after several days, while those stored in a solution buffered to pH 7.4 remained red for months.

Further study of the capsules made in this example indicate that they have a ratio of wall volume to capsule volume on the order of 0.028. When t is the wall thickness and D is the diameter, the ratio of wall volume to capsule volume is given by:

$$R = \frac{V_{wall}}{V_{capsule}} \simeq \frac{\pi D^2 t}{\pi/6 \, D^3} = 6 \, t/D$$

The capsules had an average wall thickness (t) of 700 Å or $0.07\mu$ and an average diameter (D) of $15\mu$. Hence $R \approx 6 \times 0.07/15$ or 0.028. Given that nylon has a density approximately equal to 1, 28 mg of nylon would be necessary to form the solid membranes per ml of capsules produced. The total amount of diamine present, as can be calculated from the concentration used, is 1.5 mM/ml or 174 mg/ml. Since the nylon wall is 46% by weight diamine, 12.9 mg of diamine, or about 7.5% of the total, would be necessary to form a solid nylon wall. Since, however, the acid chloride is the reaction limiting constituent and the ratio of diamine/diacid chloride was at best 50/1, the upper limit of nylon produced is on the order of 2.0% of the total diamine. This indicates that the membranes produced are most likely sponge-like with an open cell structure.

These capsules were impermeable to hemoglobin (mw≈68,000) but permeable to insulin (mw≈12,000, half equilibrium time between 2 and 3 minutes). A comparison of the half time for insulin with those for low molecular weight substances such as those given in Table I indicates a non linear relationship. It is believed that this phenomenon is caused by the steric properties or charge state of the insulin molecules.

EXAMPLE 2

The procedure was the same as that given in Example 1 except a solution consisting of one part 1 M 4,4' diaminostilbene, 2,2' disulfonic acid (Pfaltz and Bauer, Inc.) in isotonic, pH 7.4, phosphate buffer plus 10 parts 3 M hexanediamine carbonate added to an equal volume of hemolysate was substituted for diamine-DBDSA in the hemolysate solution. The capsules produced exhibited properties similar to those of Example 1.

EXAMPLE 3

The procedure is the same as that given in Example 1 except for the following. DBDSA is not included in the hemolysate solution, and the quantity of the acid chloride used in both polymerization steps, i.e., 0.35 ml acid chloride per ml of hemolysate-diamine solution, is the same. The acid halide is added in equal increments during each polymerization at 30 second intervals instead of all at once at the beginning of polymerization. This procedure keeps the local concentration of the acid chloride low and produces a high quality membrane. Percent enzyme yield is comparable to that described in Example 1.

EXAMPLE 4

Capsules were made with terephthaloyl chloride and hexanediamine containing 2,5 diaminobenzenesulfonic acid using the same procedure as that disclosed in Example 1, except 2,5 diaminobenzenesulfonic acid was added to the hexanediamine instead of DBDSA. The capsules produced exhibited properties similar to those of Example 1.

EXAMPLE 5

Sebacyl chloride-hexanediamine carbonate microcapsules were produced using the procedure of Example 1 except that sebacyl chloride was substituted for terephthaloyl chloride and no DBDSA was used. This procedure produced microcapsules with properties similar to those of the microcapsules of Example 1.

EXAMPLE 6

Sebacyl chloride-lysine capsules were prepared by the method given in Example 5 except either 3 M lysine or a solution consisting of an equal volume of 3 M hexanediamine carbonate and 3 M lysine was substituted for the 3 M hexanediamine carbonate. A few microcapsules produced by this method were leaky and unsatisfactory. Others exhibited properties similar to those produced in Example 1.

EXAMPLE 7

1.5 ml of bovine albumin (30%) is added to 1 ml of the DBDSA-Hexanediamine carbonate solution of Example 1 together with 0.4 ml 36% KCl and 0.1 ml 2.9 M tetraethylenepentamine (previously adjusted to pH 9.5 with HCl). 4.0 ml of SPAN 85 and 10 ml of the hexane-chloroform solvent of Example 1 is then added to the mix and an emulsion is produced, in 1–2 minutes, by vigorous stirring using a magnetic stirring bar. 0.4 ml of terephthaloyl chloride solution (0.5 M in hexane-chloroform solvent of Example 1) is added in 0.1 ml increments every 30 seconds, followed by additional 0.1 ml additions every minute for the next 6 minutes.

After centrifuging to separate the capsules, the supernatant is discarded, and the raw microcapsules are resuspended in cyclohexane containing 5% SPAN 85. 0.7 ml terethaloyl chloride are added, and the suspension is stirred for 3 minutes. After separation of the phases by centrifugation, the microcapsules are washed once in pure cyclohexane and subjected to final washing and recovery as indicated in Example 1.

Labile biological materials, including enzymes, may be dissolved in the albumin solution as desired. The tetraethylenepentamine helped to cross-link the polymer to form strong, uniform pore size semipermeable membranes.

While the foregoing examples are limited to polycondensation systems which include a diacid halide and a diamine to produce a polyamide polymer or copolymer, it will be obvious to those skilled in the art that the two step polymerization process and other teachings herein disclosed will be useful in many other prior art encapsulating processes. By astute selection of solvents, chosen in accordance with the teachings of this invention to suit particular polymer systems and particular materials to be encapsulated, those skilled in the art will have little difficulty in producing high quality capsule membranes of, for example, polyester, from a polyol and a diacid (HOOC—R—COOH) or diacid halide (ClOC—R—COCl), other polyamides, from a diamine ($H_2N$—R—$NH_2$) and a diacid, polyurea, from a diamine and a diisocyanate, polycarbonate, from a diol and an acid halide, polysulfonamide from a multifunctional sulfonyl halide and a diamine, as well as crosslinked protein, polyphthalamide, and other well-known polycondensations.

Encapsulating procedures using polyaddition reactions such as the type disclosed in, for example, Kan et al.'s U.S. Pat. No. 3,864,275, are also within the scope of this invention. Those skilled in the art will have little difficulty adapting the above-disclosed process to systems utilizing polyfunctional amines and, for example, epichlorohydrin or polyesters containing epoxy groups.

The invention may be embodied in other specific forms without departing from the spirit or essential characteristics thereof. The present embodiment and examples are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A process for encapsulating a chemically active core material in a porous capsule membrane from which the active core material cannot diffuse, said membrane comprising a polymer selected from the group consisting of polyamides, polyesters, polyureas, polycarbonates, and polysulfonamides, said process comprising the steps of:
    1. preparing a solution of a first monomer and said core material in a first solvent selected from the group consisting of water and hydrophilic solvents, said first monomer being selected from the group consisting of polyols and diamines;
    2. emulsifying said solution in a hydrophobic solvent in which the first monomer is slightly soluble to produce a hydrophilic discontinuous phase;
    3. adding a second monomer selected from the group consisting of diacids, diacid halides, diisocyanates, and multifunctional sulfonyl halides to said emulsion to cause an interfacial polymerization reaction between the first and second monomers at the interface of the phases of the emulsion to form macroporous polymeric capsule membranes about the members of the discontinuous phase;
    4. separating the capsules produced in step 3 from the hydrophobic solvent to terminate the polymerization reaction;
    5. resuspending the capsules in a liquid, said liquid being selected to be less soluble with said first monomer than said hydrophobic solvent;
    6. adding a second portion of said second monomer to the resuspension to cause further polymerization at said capsule membranes to strengthen said membranes and to render them microporous yet impermeable to said core material; and
    7. quenching the polymerization reaction in the resuspension.

2. The process of claim 1 further characterized by the step of adding an emulsifying agent to said system before said emulsifying step.

3. The process of claim 2 further characterized by the step of adding an emulsifying agent to said liquid.

4. The process of claim 1 wherein said first solvent is water.

5. The process of claim 1 wherein said hydrophobic solvent is a solution of cyclohexane and chloroform.

6. The process of claim 5 wherein said solution comprises 80% cyclohexane and 20% chloroform.

7. The process of claim 1 wherein said liquid is cyclohexane.

8. The process of claim 1 wherein said first monomer is a polyamine.

9. The process of claim 8 wherein said second monomer is a diacid halide.

10. The process of claim 9 wherein said diacid halide is a diacid chloride.

11. The process of claim 10 wherein the ratio of the concentration of said polyamine and said diacid chloride in their respective solvents is on the order of 100 to 1.

12. The process of claim 11 wherein the ratio of the concentration of said polyamine and said diacid chloride in their respective solvents in said resuspension is less than 60 to 1.

13. The process of claim 10 wherein the quantity of said acid chloride used is added in fractions at regular time intervals over the duration of the polymerization.

14. The process of claim 9 wherein said polyamine is chosen from the group consisting of 1,6 hexanediamine, lysine, 4,4′ diamino, 2,2′ biphenyl disulfonic acid, 4,4′ diamino stilbene 2,2′ disulfonic acid, 2,5 diaminobenzenesulfonic acid, tetraethylenepentamine, and mixtures thereof.

15. The process of claim 9 wherein said diacid chloride is chosen from the group consisting of sebacyl chloride, terephthaloyl chloride, and mixtures thereof.

16. The process of claim 1 wherein the pH of the phase containing said chemically active core material is maintained between 5 and 9.

17. The process of claim 16 wherein said chemically active core material is a labile biological substance.

18. The process of claim 17 wherein said substance is hemoglobin, said hemoglobin being prepared by removing water from red blood cells by exposing said cells to hypertonic saline solution, said saline solution being on the order of 1.5% salt by weight, to enable hemoglobin concentrations up to 30 g/dl to be prepared.

19. The process of claim 17 wherein said substance is an enzyme.

20. The process of claim 19 wherein said enzyme is chosen from the group consisting of LDH, GOT, urease, and $\beta$-glucuronidase.

21. A process for encapsulating a labile biological material within a semipermeable membrane, said process comprising the steps of:
    1. preparing an aqueous phase having a pH between 5 and 9 and containing an operative biological material and a diamine monomer;
    2. emulsifying the aqueous phase in a hydrophobic solvent in which the diamine is slightly soluble to produce an aqueous discontinuous phase;
    3. adding a diacid halide to said emulsion to cause a polymerization reaction at the interface of the phases of the emulsion and to form macroporous polymeric capsule membranes about the members of the discontinuous phase;
    4. separating the capsules produced in step 3 form the hydrophobic solvent to terminate the polymerization reaction;

5. resuspending the capsules in a liquid, said liquid being selected to be less soluble with said diamine than said hydrophobic solvent;
6. adding a second portion of diacid halide to the resuspension to cause further polymerization at said capsule membranes to strengthen said membranes and to render them microporous yet impermeable to said biological material; and
7. quenching the polymerization reaction in the resuspension.

22. The process of claim 21 wherein said labile biological material is an enzyme.

23. The process of claim 21 wherein said labile biological material is hemoglobin.

24. The process of claim 23 wherein said hemoglobin is prepared by removing water from red blood cells by exposing said cells to hypertonic saline solution, said saline solution being on the order of 1.5% salt by weight, to enable hemoglobin concentrations up to 30 g/dl to be prepared.

25. The process of claim 21 wherein said diamine is chosen from the group consisting of 1,6 hexanediamine, lysine, 4,4' diamino, 2,2' biphenyl disulfonic acid, 4,4' diamino stilbene 2,2' disulfonic acid, 2,5 diaminobenzenesulfonic acid, and mixtures thereof.

26. The process of claim 21 wherein said diacid halide is a diacid chloride.

27. The process of claim 26 wherein said diacid chloride is chosen from the group consisting of sebacyl chloride, terephthaloyl chloride and mixtures thereof.

28. The process of claim 21 further characterized by the step of adding an emulsifying agent to said hydrophobic solvent before emulsifying.

29. The process of claim 28 wherein said emulsifying agent is sorbitan trioleate.

30. The process of claim 21 wherein the pH of said aqueous phase is set by passing $CO_2$ therethrough.

31. The process of claim 21 wherein said hydrophobic solvent is a mixture of cyclohexane and chloroform.

32. The process of claim 31 wherein said hydrophobic solvent is a mixture, by volume, of 80% cyclohexane and 20% chloroform.

33. The process of claim 21 wherein said liquid is cyclohexane.

34. The process of claim 21 wherein the quenching step is accomplished by adding sorbitan monolaurate in a hypertonic solution buffered to have a pH close to 7.

35. The process of claim 21 wherein a polyamine is added to said diamine monomer before adding the hydrophobic solvent.

36. The process of claim 36 wherein said polyamine is tetraethylenepentamine.

37. The process of claim 35 wherein said polyamine is adjusted to have a pH between 5 and 9 before it is added to said diamine monomer.

38. The process as set forth in claim 21 wherein the hydrophobic solvent is relatively non-denaturing to said biological material.

39. The process as set forth in claim 21 wherein the diacid halide added in step 3 is added in increments as the polymerization reaction proceeds.

* * * * *

UNITED STATES PATENT AND TRADEMARK OFFICE
CERTIFICATE OF CORRECTION

PATENT NO. : 4,324,683
DATED : April 13, 1982
INVENTOR(S) : Franklin Lim and Richard D. Moss It is certified that error appears in the above-identified patent and that said Letters Patent are hereby corrected as shown below:

Col. 3, line 11, "any" should be --many--.

Col. 4, line 12, "aseable" should be --usable--.

Col. 8, line 21, "DBSA" should be --DBDSA--.

Col. 8, line 43, "of" should be --or--.

Col. 12, line 47, "terethaloyl" should be --terephthaloyl--.

Col. 14, Claim 21, No. 4, "form" should be --from--.

Col. 16, Claim 36, line 1, "36" should be --35--.

Signed and Sealed this

Twentieth Day of July 1982

[SEAL]

Attest:

GERALD J. MOSSINGHOFF

Attesting Officer

Commissioner of Patents and Trademarks